United States Patent
Miller et al.

(10) Patent No.: US 9,737,538 B2
(45) Date of Patent: Aug. 22, 2017

(54) SOLID DISPERSIONS OF LOW-WATER SOLUBILITY ACTIVES

(71) Applicant: Bend Research, Inc., Bend, OR (US)

(72) Inventors: Warren K. Miller, Bend, OR (US); Michael M. Morgen, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

(21) Appl. No.: 14/767,264

(22) PCT Filed: Feb. 12, 2014

(86) PCT No.: PCT/US2014/015959
§ 371 (c)(1),
(2) Date: Aug. 11, 2015

(87) PCT Pub. No.: WO2014/126969
PCT Pub. Date: Aug. 21, 2014

(65) Prior Publication Data
US 2015/0374827 A1    Dec. 31, 2015

Related U.S. Application Data

(60) Provisional application No. 61/763,863, filed on Feb. 12, 2013, provisional application No. 61/792,240, filed on Mar. 15, 2013.

(51) Int. Cl.
*A61K 31/517*     (2006.01)
*A61K 9/14*     (2006.01)

(52) U.S. Cl.
CPC ............ *A61K 31/517* (2013.01); *A61K 9/146* (2013.01)

(58) Field of Classification Search
CPC ............................. A61K 9/146; A61K 31/517
USPC ..................................................... 514/266.4
See application file for complete search history.

(56) References Cited

U.S. PATENT DOCUMENTS

| | | | |
|---|---|---|---|
| 2008/0262107 A1* | 10/2008 | Babcock | A61K 9/146 514/781 |
| 2009/0061009 A1 | 3/2009 | Schwarz et al. | |
| 2010/0029667 A1* | 2/2010 | Ketner | A61K 9/1617 514/252.01 |

FOREIGN PATENT DOCUMENTS

| EP | 2 578 209 A1 | 4/2013 |
|---|---|---|
| WO | WO 2008/047201 | 4/2008 |
| WO | WO 2009/076761 | 6/2009 |

OTHER PUBLICATIONS

International Search Report and Written Opinion Issued by European Patent Office, on May 6, 2014, for PCT Patent Application No. PCT/US2014/015959, 7pp.

* cited by examiner

*Primary Examiner* — T. Victor Oh
(74) *Attorney, Agent, or Firm* — Klarquist Sparkman, LLP

(57) ABSTRACT

Disclosed are compositions including a solid dispersion comprising a dispersion polymer, a basic low-water solubility active, and an anionic counterion, as well as methods of making and using the compositions.

19 Claims, No Drawings

SOLID DISPERSIONS OF LOW-WATER SOLUBILITY ACTIVES

CROSS REFERENCE TO RELATED APPLICATIONS

This is the U.S. National Stage of International Application No. PCT/US2014/015959, filed Feb. 12, 2014, which was published in English under PCT Article 21(2), which in turn claims the benefit of U.S. Provisional Application No. 61/763,863, filed Feb. 12, 2013, and U.S. Provisional Application No. 61/792,420, filed Mar. 15, 2013, each of which is incorporated herein by reference.

TECHNICAL FIELD

Disclosed are compositions including solid dispersions comprising a dispersion polymer, a basic low-water solubility active, and an anionic counterion, as well as methods of making and using the compositions.

BACKGROUND

Salt forms of low-water solubility actives are known in the art. The typical goal of forming a salt form is to improve the water solubility of the active, so as to improve its bioavailability when taken orally.

Solid dispersions of low-water solubility actives and polymers may improve the bioavailability of the active by enhancing the concentration of the active in the gastrointestinal (GI) tract, or by increasing the dissolution rate of the active.

The inventors have found that there is a continuing need to develop methods and compositions to improve the bioavailability of low-water solubility actives.

SUMMARY

Embodiments of compositions including a solid dispersion comprising a dispersion polymer, a basic low-water solubility active, and an anionic counterion are disclosed. Methods of making and using the compositions are also disclosed.

In one embodiment, a composition comprising a solid dispersion comprising (a) a dispersion polymer; (b) a basic low-water solubility active having a pKa, wherein said active in said solid dispersion is substantially non-crystalline; and (c) an anionic counterion for said active is disclosed. By "substantially non-crystalline" is meant at least 90 wt % non-crystalline, or less than 10 wt % crystalline. The dispersion polymer, the basic low-water solubility active and the anionic counterion collectively constitute at least 50 wt % of the dispersion. The anionic counterion has a molecular weight of at least 200 Daltons, a Log P value of at least 2, and a pKa that is at least 1.5 units less than the highest pKa of the active. The composition comprises at least 80% of the stoichiometric amount of the anionic counterion necessary to form a salt form of the basic low-water solubility active.

DETAILED DESCRIPTION

The present disclosure relates to compositions including a solid dispersion comprising a dispersion polymer, a basic low-water solubility active, and an anionic counterion. Various embodiments are disclosed herein. The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

As used in this application and in the claims, "pKa" is defined as the negative logarithm of the ionization constant (K) of an acid, which is the pH of a solution in which half of the acid molecules are ionized. The term "pKb" is defined as the negative logarithm of the ionization constant (K) of a base. As one of ordinary skill in the art will understand, the pKb of a base is equal to 14-pKa of an acid. Thus, as used herein and in the claims, the pKa of a basic active is equal to 14-pKb of the base. Thus, if the anionic counterion has a pKa that is at least 1.5 units less than the lowest pKb of the active, that is equivalent to saying that the anionic counterion has a pKa that is at least 1.5 units less than the highest pKa of the active.

Active Agents

Embodiments of the disclosed compositions are suitable for use with any biologically active compound desired to be administered to a patient in need of the active agent. The compositions may contain one or more active agents. As used herein, by "active" or "active agent" is meant a drug, medicament, pharmaceutical, therapeutic agent, nutraceutical, or other compound that may be desired to be administered to the body. The active may be a "small molecule," generally having a molecular weight of 2000 Daltons or less. The active may also be a "biological active." Biological actives include proteins, antibodies, antibody fragments, peptides, oligonucleotides, vaccines, and various derivatives of such materials. In one embodiment, the active is a small molecule. In another embodiment, the active is a biological active. In still another embodiment, the active is a mixture of a small molecule and a biological active.

By "basic active" is meant an active which contains one or more protonatable groups. In one embodiment, a basic active has a pKb in the range of 3 to 14. In another embodiment, a basic active has a pKb in the range of 3 to 10 or in the range of 4 to 8. In one embodiment, the basic active has a pKa in the range of 0 to 11. In another embodiment, the basic active has a pKa in the range of 4 to 11, or in the range of 6 to 10.

A "basic low-water solubility active" as employed herein is an active that is essentially totally water-insoluble or poorly water-soluble at any pH in the range of pH 5.0 to pH 7.0. In one embodiment, the basic low-water solubility active has a water solubility of less than 5 mg/mL at any pH in the range of pH 5.0 to pH 7.0. The active agent may have an even lower water solubility at any pH in the range of pH 5.0 to pH 7.0, such as less than 3 mg/mL, less than 2 mg/mL, less than 1 mg/mL, less than 0.1 mg/mL, and even less than 0.01 mg/mL.

The active agent should be understood to include the non-ionized form of the active. In one embodiment, the active includes pharmaceutically acceptable forms of the active. The term "pharmaceutically acceptable" refers to a substance that can be taken into a subject without significant adverse toxicological effects on the subject. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, and prodrugs of the active.

Examples of classes of active agents include, but are not limited to, compounds for use in the following therapeutic areas: antihypertensives, antianxiety agents, antiarrhythmia agents, anticlotting agents, anticonvulsants, blood glucose-lowering agents, decongestants, antihistamines, antitussives, antineoplastics, anticancer agents, antitumor agents, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, bronchodilators, glucocorticoids, steroids, and antiviral agents.

Anionic Counterions

The compositions also include an anionic counterion. By "anionic counterion" is meant that the counterion has a pKa that is at least 1.5 units less than the lowest pKb of the active. (This is equivalent to saying that the anionic counterion has a pKa that is at least 1.5 units less than the highest pKa of the active.) In one embodiment, the pKa of the anionic counterion is at least 2 units less than the lowest pKb of the active (or the pKa of the anionic counterion is at least 2 units less than the highest pKa of the active). In another embodiment, the pKa of the anionic counterion is at least 3 units less than the lowest pKb of the active (or the pKa of the anionic counterion is at least 3 units less than the highest pKa of the active).

In one embodiment, the anionic counterion has a pKa of 5 or lower. In another embodiment, the anionic counterion has a pKa of 4 or lower. In still another embodiment, the anionic counterion has a pKa of 3 or lower. In yet another embodiment, the aninonic counterion has a pKa of 2 or lower.

In one embodiment, the anionic counterion is lipophilic, having a Log P value of at least 2, or at least 3, or even at least 4. The Log P value, defined as the base 10 logarithm of the ratio of (1) the drug concentration in an octanol phase to (2) the drug concentration in a water phase when the two phases are in equilibrium with each other, is a widely accepted measure of hydrophobicity. The Log P value may be measured experimentally or calculated using methods known in the art. The Log P value may be estimated experimentally by determining the ratio of the drug solubility in octanol to the drug solubility in water. When using a calculated value for the Log P value, the highest value calculated using any generally accepted method for calculating Log P is used. Calculated Log P values are often referred to by the calculation method, such as Clog P, Alog P, and Mlog P. The Log P value may also be estimated using fragmentation methods, such as Crippen's fragmentation method (*J. Chem. Inf. Comput. Sci.,* 27,21 (1987)); Viswanadhan's fragmentation method (*J. Chem. Inf. Comput. Sci.,*29,163 (1989)); or Broto's fragmentation method (*Eur. J. Med. Chem.-Chim. Theor.,* 19,71 (1984). In some embodiments, the Log P value is calculated by using the average value estimated using Crippen's, Viswanadhan's, and Broto's fragmentation methods.

In one embodiment, the anionic counterion comprises at least 8 carbon atoms, and at least one acidic group. In another embodiment, the anionic counterion comprises at least 10 carbon atoms and at least one acidic group. In yet another embodiment, the anionic counterion comprises at least 12 carbon atoms and at least one acidic group. In still another embodiment, the anionic counterion comprises at least 14 carbon atoms and at least one acidic group. In another embodiment, the anionic counterion comprises at least 16 carbon atoms and at least one acidic group. In still another embodiment, the anionic counterion comprises at least 18 carbon atoms and at least one acidic group. In one embodiment, the group is selected from sulfate, phosphate, and carboxylate groups. In another embodiment, the anionic counterion comprises at least 18 carbon atoms, and at least one group selected from sulfate, phosphate, and carboxylate.

In another embodiment, the anionic counterion has a pKa that is at least 1.5 units less than the highest pKa of the active, a molecular weight that is at least 200 Daltons, and a Log P value that is at least 2. In still another embodiment, the anionic counterion has a pKa that is at least 2 units less than the highest pKa of the active, a molecular weight that is at least 300 Daltons, and a Log P value that is at least 3.

The basic low-water solubility active and the anionic counterion are capable of forming a salt form. By "capable of forming a salt form" means that the basic low-water solubility active and the anionic counterion, under the proper conditions, will react to form the corresponding salt form with the active, meaning that the proton on the basic low-water solubility active has been replaced with the corresponding counterion. In one embodiment, at least 80 wt % of the basic-low water solubility active has reacted with the anionic counterion to form the corresponding salt form. In another embodiment, at least 90 wt % of the basic-low water solubility active has reacted with the anionic counterion to form the corresponding salt form. In yet another embodiment, at least 95 wt % of the basic-low water solubility active has reacted with the anionic counterion to form the corresponding salt form. In still another embodiment, essentially all of the basic-low water solubility active has reacted with the anionic counterion to form the corresponding salt form. In another embodiment, the salt form of the active and the anionic counterion in pure form has an aqueous solubility, when measured in an aqueous solution containing 0.01 M HCl at pH 2.0 at 37° C., that is less than the aqueous solubility of the corresponding HCl salt form when measured in an aqueous solution containing 0.01 M HCl at pH 2.0 at 37° C. The term "pure form" means that the salt form is not combined with another component, i.e., that the salt form consists essentially of, or consists of the active and the anionic counterion. In one embodiment, the salt form of the active and the anionic counterion in pure form has an aqueous solubility that is less than 0.9-fold the aqueous solubility of the corresponding HCl salt form when measured in an aqueous solution containing 0.01 M HCl at pH 2.0 at 37° C. In another embodiment, the salt form of the active and the anionic counterion in pure form has an aqueous solubility that is less than 0.85-fold the aqueous solubility of the corresponding HCl salt form when measured in an aqueous solution containing 0.01 M HCl at pH 2.0 at 37° C.

In still another embodiment, the salt form of the active and the anionic counterion in pure form has an aqueous solubility, when measured in an aqueous solution containing 0.01 M HCl at pH 2.0 at 37° C., that is less than the aqueous solubility of the free base of the active when measured in an aqueous solution containing 0.01 M HCl at pH 2.0 at 37° C. In one embodiment, the salt form of the active and the anionic counterion in pure form has an aqueous solubility that is less than 0.9-fold the aqueous solubility of the free base when measured in an aqueous solution containing 0.01 M HCl at pH 2.0 at 37° C. In another embodiment, the salt form of the active and the anionic counterion in pure form has an aqueous solubility that is less than 0.85-fold the aqueous solubility of the free base of the active when measured in an aqueous solution containing 0.01 M HCl at pH 2.0 at 37° C.

In one embodiment, the salt form of the active and the anionic counterion in pure form has a melt temperature that is at least 10° C. less than the corresponding HCl salt form of the active. In another embodiment, the salt form of the active and the anionic counterion in pure form, has a melt temperature that is at least 20° C. less than the corresponding HCl salt form of the active, or at least 30° C. less than the corresponding HCl salt form of the active. In one embodiment, the counterion, when associated with the active, is substantially non-crystalline, i.e., at least 90 wt % of the counterion, when associated with the active, is non-crystalline. In another embodiment, the counterion, when associated with the active, is primarily non-crystalline, i.e., at least 80 wt %. In yet another embodiment, a majority (i.e., at least 60 wt %) of the counterion, when associated with the active, is non-crystalline. Thus, less than 10 wt %, less than 20 wt %, or less than 40 wt % of the counterion, when associated with the active, may be crystalline.

In another embodiment, the salt form of the active and the anionic counterion in pure form results in a melt temperature that is at least 10° C. less than the melt temperature of the free base of the active. In another embodiment, the salt form of the active and the anionic counterion in pure form results in a melt temperature that is a least 20° C. less than the melt temperature of the free base of the active, or at least 30° C. less than the melt temperature of the free base of the active.

In one embodiment, the salt form of the active and the anionic counterion in pure form results in at least one of (i) a melt temperature that is at least 10° C. less than the corresponding HCl salt form of the active, (ii) a melt temperature that this at least 10° C. less than the free base of the active, or (iii) both (i) and (ii).

In one embodiment, the anionic counterion is selected from 1,4-bis(2-ethylhexoxy)-1,4-dioxobutane-2-sulfonate (also known as docusate), cholesteryl sulfate, cholesteryl phosphate, tocopherol sulfate, tocopherol phosphate, 4,4'-methylenebis(3-hydroxy-2-naphthoic acid) (pamoic acid), 2,6-di-tert-butylnaphthalene-1-sulfonic acid, 2,6-di-tert-butylnaphthalene-1,5-disulfonic acid, 1,4-dicyclohexyloxy-1,4-dioxobutane-2-sulfonic acid, 1,4-diisopentyloxy-1,4-dioxobutane-2-sulfonic acid, and combinations thereof. The foregoing list is not intended to indicate that all embodiments are equivalent and/or equally suitable.

In one embodiment, the anionic counterion is 1,4-bis(2-ethylhexoxy)-1,4-dioxobutane-2-sulfonate, having the structure:

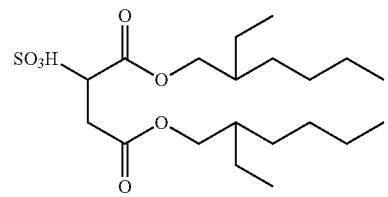

In one embodiment, the anionic counterion is cholesteryl sulfate, having the structure:

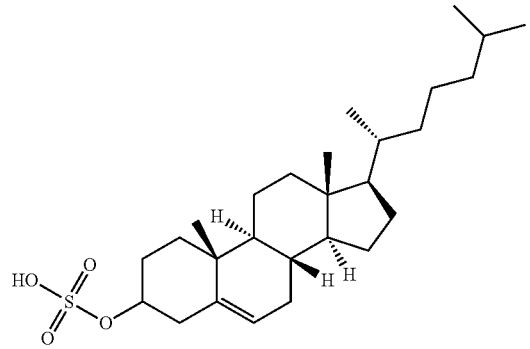

In one embodiment, the anionic counterion is cholesteryl phosphate, having the structure:

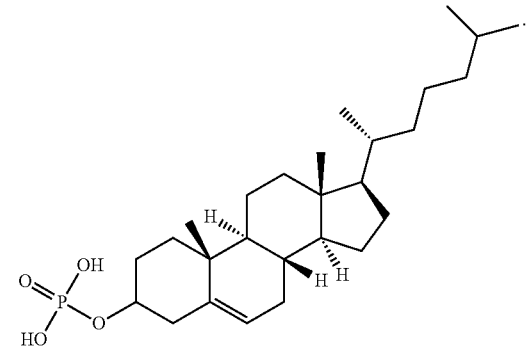 [SMILES: CC(C)CCC[C@@H](C)[C@H]1CC[C@H]2[C@@H]3CC=C4CC(OP(=O)(O)O)CC[C@]4(C)[C@H]3CC[C@]12C]

In one embodiment, the anionic counterion is tocopherol sulfate, having the structure:

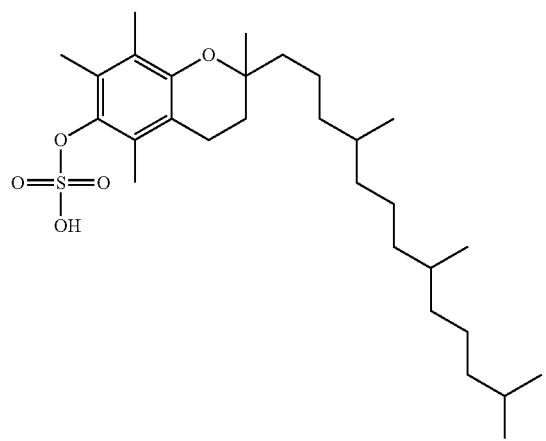 [SMILES: Cc1c(C)c2c(c(C)c1OS(=O)(=O)O)CCC(C)(CCCC(C)CCCC(C)CCCC(C)C)O2]

In one embodiment, the anionic counterion is tocopherol phosphate, having the structure:

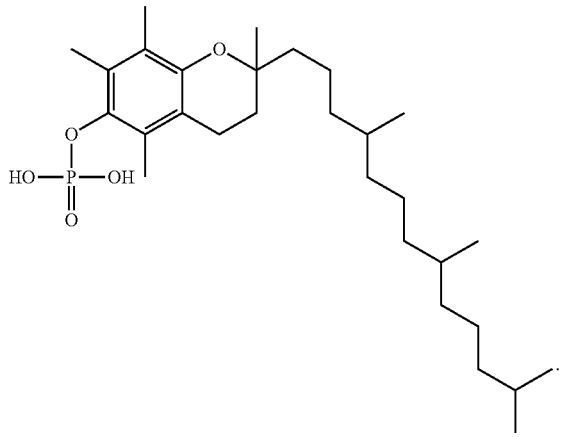 [SMILES: Cc1c(C)c2c(c(C)c1OP(=O)(O)O)CCC(C)(CCCC(C)CCCC(C)CCCC(C)C)O2]

In one embodiment, the anionic counterion is pamoic acid, having the structure:

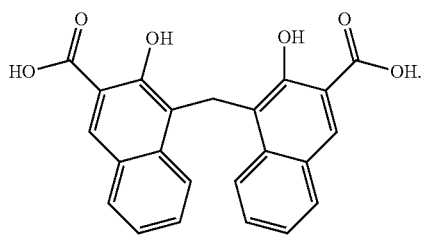 [SMILES: O=C(O)c1cc2ccccc2c(Cc2c(O)c(C(=O)O)cc3ccccc23)c1O]

In one embodiment, the anionic counterion is 2,6-di-tert-butylnaphthalene-1-sulfonic acid, having the structure:

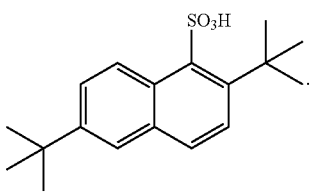 [SMILES: CC(C)(C)c1ccc2c(S(=O)(=O)O)c(C(C)(C)C)ccc2c1]

In one embodiment, the anionic counterion is 2,6-di-tert-butylnaphthalene-1,5-disulfonic acid, having the structure:

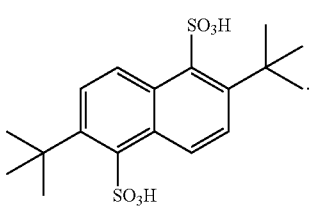 [SMILES: CC(C)(C)c1ccc2c(S(=O)(=O)O)c(C(C)(C)C)ccc2c1S(=O)(=O)O]

In one embodiment, the anionic counterion is 1,4-dicyclohexyloxy-1,4-dioxobutane-2-sulfonic acid, having the structure:

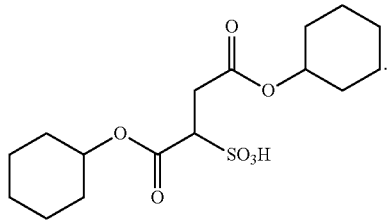 [SMILES: O=C(CC(C(=O)OC1CCCCC1)S(=O)(=O)O)OC1CCCCC1]

In one embodiment, the anionic counterion is 1,4-diisopentyloxy-1,4-dioxobutane-2-sulfonic acid, having the structure:

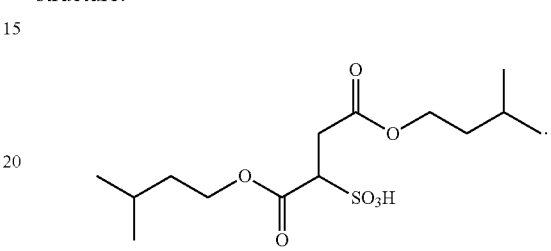

Table 1 lists some of the properties of the anionic counterions.

TABLE 1

Properties of Anionic Counterions.

| Anionic Counterion | Formula | Molecular Weight (Daltons) | pKa | Log P (Calculated) |
|---|---|---|---|---|
| 1,4-bis(2-ethylhexoxy)-1,4-dioxobutane-2-sulfonate | $C_{20}H_{38}O_7S$ | 422.5 | <1 estimated | 4.84 |
| Cholesteryl sulfate | $C_{27}H_{46}O_4S$ | 466.7 | <1 estimated | >4 estimated |
| Cholesteryl phosphate | $C_{27}H_{46}O_4P$ | 466.6 | <2 estimated | >7 estimated |
| Tocopherol phosphate | $C_{29}H_{51}O_5P$ | 510.6 | <2 estimated | 10.0 |
| Tocopherol sulfate | $C_{29}H_{50}O_5S$ | 510.8 | <1 estimated | 9.1 |
| 4,4'-methylenebis (3-hydroxy-2-naphthoic acid) (pamoic acid) | $C_{23}H_{16}O_6$ | 388 | 2.5, 3.1 | 4.46 |
| 2,6-di-tert-butylnaphthalene-1-sulfonic acid | $C_{18}H_{24}O_3S$ | 320 | −2.48 | 5.6 |
| 2,6-di-tert-butylnaphthalene-1,5-disulfonic acid | $C_{18}H_{24}O_6S_2$ | 400.5 | −2.32, −3.05 | 4.76 |
| 1,4-dicyclohexyloxy-1,4-dioxobutane-2-sulfonic acid | $C_{16}H_{26}O_7S$ | 362.4 | <1 estimated | 2.13 |
| 1,4-diisopentyloxy-1,4-dioxobutane-2-sulfonic acid | $C_{14}H_{26}O_7S$ | 338.4 | <1 estimated | 2.18 |

In one embodiment, the composition comprises at least 80% of the stoichiometric amount of the anionic counterion necessary to form a salt form with the basic low-water solubility active. In another embodiment, the composition comprises at least 90% of the stoichiometric amount of the anionic counterion necessary to form a salt form of the basic low-water solubility active. In still another embodiment, the composition comprises at least 100% of the stoichiometric amount of the anionic counterion necessary to form a salt form of the basic low-water solubility active. In another embodiment, the composition comprises a stoichiometric excess of the anionic counterion relative to the basic low-water solubility active.

In one embodiment, the salt form of the active and the counterion may be formed by adding a stoichiometric quantity of the counterion to the active in an appropriate solvent. In another embodiment, a stoichiometric excess of the counterion is added to the active in an appropriate solvent. The inventors have found that including a stoichiometric excess of the anionic counterion can improve the performance when the composition is administered to an aqueous use environment, such as in vivo and in vitro use environments.

Dispersion Polymers

Embodiments of the disclosed compositions comprise at least one dispersion polymer, i.e., a polymer in which the basic low-water solubility active and the anionic counterion are dispersed. Exemplary polymers include polyvinyl pyrrolidone (PVP), polyethyleneoxide (PEO), polyethylene glycol (PEG), poly(vinyl pyrrolidone-co-vinyl acetate) (PVP-VA), polyoxyethylene-polyoxypropylene block copolymers (also referred to as poloxamers), graft copolymers comprised of polyethylene glycol, polyvinyl caprolactam and polyvinyl acetate (such as Soluplus®), polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose (HPMC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1 (e.g., Eudragit® L100, Evonik Industries AG), poly(methacrylic acid-co-methyl methacrylate) 1:2 (e.g., Eudragit® S100), poly(methacrylic acid-co-ethyl acrylate) 1:1 (e.g., Eudragit® L100-55), and mixtures thereof. The foregoing list is not intended to indicate that all embodiments are equivalent and/or equally suitable.

In still another embodiment, the polymer is selected from HPMCAS, HPMCP, CAP, CAT, CMEC, HPMC, HPMCAP, HPMCAT, CAS, MCAS, dextran, Eudragit® L100, Eudragit® S100, Eudragit® L100-55, and mixtures thereof.

In certain embodiments, the polymer is a cellulosic polymer selected from hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose (HPMC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), and mixtures thereof. In other embodiments, the polymer is selected from HPMCAS, HPMCP, CAP, CAT, CMEC, HPMC, HPMCAP, HPMCAT, CAS, MCAS, and mixtures thereof. In another embodiment, the polymer is selected from HPMCAS, HPMCP, CAP, CAT, CMEC, HPMC, and mixtures thereof.

In certain embodiments, the polymer has a high glass-transition temperature (Tg) when measured at a relative humidity (RH) of 50%. The Tg of the polymer at 50% RH may be at least 50° C., at least 60° C., at least 70° C., or at least 80° C. The inventors have determined that selecting a polymer having a high Tg, results in a dispersion with a high Tg at 50% RH, leading to improved physical stability of the dispersion. The glass transition temperature, Tg, is the temperature at which an amorphous (non-crystalline) solid, such as glass or a polymer, becomes brittle or strong on cooling, or soft or pliable on heating. Tg can be determined, for example, by differential scanning calorimetry (DSC). DSC measures the difference in the amount of heat required to raise the temperature of a sample and a reference as a function of temperature. During a phase transition, such as a change from an amorphous state to a crystalline state, the amount of heat required changes. For a solid that has no crystalline components, a single glass transition temperature indicates that the solid is homogeneous or a molecular dispersion. Relative humidity is a measure of the amount of water in air compared with the amount of water the air can hold at a particular temperature. Relative humidity may be measured, for example, through the use of psychrometric charts if both the dry bulb temperature and the wet bulb temperature of an air-water vapor mixture are known. These temperatures can be determined by using a sling psychrometer.

In one embodiment, the polymer is HPMCAS. In another embodiment, the polymer is hydroxypropyl methyl cellulose propionate succinate. In another embodiment, the polymer is CAP. In another embodiment, the polymer is CMEC. In another embodiment, the polymer is HPMC. In another embodiment, the polymer is HPMCAP. In another embodiment, the polymer is hydroxypropyl methylcellulose propionate phthalate. In another embodiment, the polymer is HPMCAT. In another embodiment, the polymer is hydroxypropyl methylcellulose propionate trimellitate. In another embodiment, the polymer is CAS. In another embodiment, the polymer is MCAS. In another embodiment, the polymer is Eudragit® L100. In another embodiment, the polymer is Eudragit® S100. In another embodiment, the polymer is Eudragit® L100-55. In another embodiment, the polymer is PVP. In another embodiment, the polymer is PVP-VA.

In certain embodiments, the dispersion of an active, anionic counterion and polymer has a glass-transition temperature of at least 30° C. when measured at 50% RH. In other embodiments, the disclosed dispersions have a glass-transition temperature of at least 40° C. at 50% RH, at least 50° C. at 50% RH, at least 60° C. at 50% RH, at least 70° C. at 50% RH, or even at least 80° C. at 50% RH. The inventors have found that dispersions meeting these criteria have improved physical stability compared to dispersions that do not meet these criteria.

Compositions

Embodiments of the disclosed compositions comprise a dispersion comprising a dispersion polymer, a basic low-water solubility active, and an anionic counterion. In one embodiment, the dispersion polymer, the basic low-water solubility active, and the anionic counterion collectively constitute at least 50 wt % of the dispersion. In another embodiment, the dispersion polymer, the basic low-water solubility active, and the anionic counterion collectively constitute at least 80 wt % of the dispersion. In still another embodiment, the dispersion polymer, the basic low-water solubility active, and the anionic counterion collectively constitute at least 90 wt % of the dispersion.

In one embodiment, the disclosed compositions consist essentially of a dispersion polymer, a basic low-water solubility active, and an anionic counterion. In other embodiments, the disclosed compositions consist of a dispersion polymer, a basic low-water solubility active, and an anionic counterion.

In one embodiment, the amount of basic low-water solublility active in the dispersion may range from 0.01 wt % to 99 wt % active relative to the total weight of the dispersion, i.e., the combined weight of the active, the anionic counterion, and the dispersion polymer. In other embodiments, the amount of active may range from 0.1 wt % to 80 wt %, or from 0.1 to 60 wt %, or from 1 to 40 wt %. In other embodiments, the amount of active in the dispersion may be at least 1 wt %, at least 5 wt %, at least 10 wt %, at least 15 wt %, at least 20 wt %, at least 25 wt %, at least 30 wt %, at least 40 wt %, at least 45 wt %, or even at least 50 wt %.

In one embodiment, the active is present in the dispersion as a salt form of the active and the anionic counterion, which salt form is dispersed in the dispersion polymer.

In one embodiment, the active in the dispersion (and/or the salt form of the active and the anionic counterion) is present in a non-crystalline state. In one embodiment, the non-crystalline active can exist as a pure active phase (i.e., active and/or the salt form of the active and the anionic counterion), as a solid solution of active homogeneously distributed throughout the polymer, or any combination of these states or those that lie intermediate between them. A "solid solution" is formed when at least one solid component is molecularly dispersed within another solid component, resulting in a homogeneous or substantially homogeneous solid material. In one embodiment, a majority (at least 60 wt %) of the active in the dispersion is present in a non-crystalline state. In another embodiment, at least 80 wt % of the active in the dispersion is present in a non-crystalline state. In another embodiment, at least 90 wt % of the active in the dispersion is present in a non-crystalline state, i.e., the active is substantially present in a non-crystalline state. In yet another embodiment, at least 95 wt % of the active in the dispersion is present in a non-crystalline state. In still another embodiment, essentially all of the active in the dispersion is in a non-crystalline state. In one embodiment, the non-crystalline active is present as a solid solution of active homogeneously distributed throughout the polymer.

The amount of non-crystalline active in the dispersion may be measured by powder X-ray diffraction (PXRD) or modulated differential scanning calorimetry (mDSC), or any other standard quantitative measurement.

In certain embodiments, the disclosed compositions are in the form of a solid dry powder comprising a plurality of particles. As used herein, the term "particles" means small pieces of matter having characteristic diameters of less than 3000 μm. In another embodiment, the particles are granulated into granules using standard methods known in the art, such as dry granulation, wet granulation, high shear granulation, and the like.

In one embodiment, the mean size of the particles is less than 500 μm. In another embodiment, the mean size of the particles is less than 200 μm. In still another embodiment, the mean size of the particles is less than 100 μm. In one embodiment, the mean size of the particles ranges from 0.5 to 500 μm. In another embodiment, the mean size of the particles ranges from 0.5 to 200 μm. In one embodiment, the mean size of the particles ranges from 0.5 to 100 μm. In one embodiment, the mean size of the particles ranges from 10 to 100 μm. In one embodiment, the mean size of the particles ranges from 10 to 70 μm. In one embodiment, the mean size of the particles ranges from 10 to 50 μm. In one embodiment, the mean size of the particles ranges from 0.5 to 10 μm. In one embodiment, the mean size of the particles ranges from 0.5 to 7 μm.

In one embodiment, the salt form of the active with the counterion may be made and isolated, followed by forming a composition as disclosed herein. In another embodiment, the salt form of the active and the counterion may be formed in situ in an appropriate solvent, and subsequently formed into a composition as disclosed herein.

In one method of forming embodiments of the disclosed compositions, the basic low-water solubility active, anionic counterion, and polymer are mixed with a solvent to form a liquid solution or liquid suspension. The solid dispersions may then be formed from the liquid solution or suspension by any known process, including precipitation in a miscible non-solvent, emulsifying in an immiscible non-solvent, or by forming droplets followed by removal of the solvent by evaporation to produce particles.

In one embodiment, particles comprising a solid dispersion are formed by spray drying. The active, dispersion polymer, and anionic counterion may be added to a solvent. Thus, the fluid that is spray dried may be a suspension or a homogeneous solution or a combination of dissolved and suspended materials. In one embodiment, the fluid that is spray dried comprises a homogeneous solution of active, polymer, and anionic counterion dissolved together in a solvent.

The solvent may be any pharmaceutically acceptable solvent or mixture of solvents having a boiling point of less than 150° C. Suitable solvents include water, acetone, methanol, ethanol, methyl acetate, ethyl acetate, tetrahydrofuran (THF), dichloromethane, and mixtures of solvents. The foregoing list is not intended to indicate that all of the solvents are equivalent and/or equally suitable. When the spray drying solution comprises an organic solvent that is water miscible, such as acetone or methanol, water may be added to the solution. The spray drying solution is then sprayed through an atomizer such as a pressure nozzle or two-fluid nozzle into a spray drying chamber. The droplets are contacted with a heated drying gas such as dry nitrogen. Droplets dry rapidly, forming particles comprising a solid dispersion comprising the dispersion polymers, the basic low-water solubility active, and the anionic counterion. The particles exit the spray dryer and are collected, such as in a cyclone. Subsequent processes may be used to remove any residual solvent from the particles. Exemplary apparatus and procedures for forming spray-dried solid dispersions are also described in U.S. Pat. No. 8,263,128 and U.S. Publication No. 2012/0015924, each of which is incorporated herein by reference.

Thus, in some embodiments, a process for making a solid dispersion comprises: (1) adding an active, a polymer, and an anionic counterion to a solvent to form a solution or suspension, (2) directing the solution or suspension to a spray drying apparatus and atomizing the solution or suspension into droplets in the spray drying apparatus, (3) contacting the droplets with a drying gas, resulting in solidification of particles, and (4) collecting the particles. Alternatively, the process for making a solid dispersion comprises (1) forming a salt form of the basic low-water solubility active and anionic counterion, (2) adding the salt form and a dispersion polymer to a solvent to form a solution or suspension, (3) directing the solution or suspension to a spray drying apparatus and atomizing the solution or suspension into droplets in the spray drying apparatus, (4) contacting the droplets with a drying gas, resulting in solidification of particles, and (5) collecting the particles.

Methods of Use

In one embodiment, compositions comprising the disclosed dispersions can be formulated into suitable dosage forms, such as tablets, capsules, suspensions, powders for suspension, creams, transdermal patches, depots, and the like. Conventional formulation excipients may be employed in embodiments of the disclosed compositions, including those excipients well-known in the art, such as those described in Remington: The Science and Practice of Pharmacy (20th ed., 2000). Generally, excipients such as fillers, disintegrating agents, pigments, binders, lubricants, glidants, flavorants, and so forth may be used for customary purposes and in typical amounts without adversely affecting the properties of the compositions.

EXAMPLES

Active Agents

Erlotinib, also known as N-(3-ethynylphenyl)-6,7-bis(2-methoxyethoxy) quinazolin-4-amine, having the following structure, was used in the Examples.

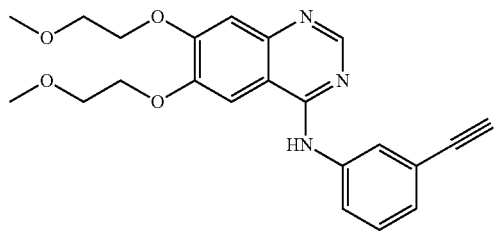 [SMILES: C#Cc1cccc(Nc2ncnc3cc(OCCOC)c(OCCOC)cc23)c1]

Erlotinib has a melt temperature of 157° C., and a glass-transition temperature of 37° C. The Log P value is 2.7, and it has a pKa of 5.42. Erlotinib has a solubility in phosphate buffered saline (pH 6.5) of about 1 µg/mL.

Example 1

A 0.226 g sample of sodium 1,4-bis(2-ethylhexoxy)-1,4-dioxobutane-2-sulfonate was placed in a 20 mL glass vessel with 10 mL tetrahydrofuran (THF) and stirred with a magnetic stir bar until completely dissolved. A 0.41 mL sample of 1.25 M HCL in methanol was added with stirring yielding a white precipitate. The mixture was chilled to about 0° C. to ensure complete precipitation of sodium chloride. The mixture was then filtered through a 0.2 micron filter to remove sodium chloride followed by an additional rinse of 10 mL THF to extract all of the 1,4-bis(2-ethylhexoxy)-1,4-dioxobutane-2-sulfonate. The solution was placed on a rotoevaporator and solvents were removed resulting in a clear film of 1,4-bis(2-ethylhexoxy)-1,4-dioxobutane-2-sulfonate in its protonated (non-ionized) form. The entire sample of the protonated 1,4-bis(2-ethylhexoxy)-1,4-dioxobutane-2-sulfonate was dissolved in 10 mL of THF and added quantitatively to a separate solution containing 200.1 mg of erlotinib free base in 10 mL THF. The resulting clear solution was stirred for several minutes. Solvent was removed by rotoevaporation. The residue was placed on a vacuum line overnight to remove residual solvent. The sample was dissolved in 10 mL of acetone and then rotoevaporated to remove solvent. The sample was dissolved a second time in 10 mL of acetone followed by rotoevaporation and was then dried overnight under vacuum. The product, erlotinib 1,4-bis(2-ethylhexoxy)-1,4-dioxobutane-2-sulfonate, was a clear syrup/glass at room temperature, and did not exhibit a melting point when analyzed by mDSC.

Dispersion 1

A solution of 0.1629 g erlotinib 1,4-bis(2-ethylhexoxy)-1,4-dioxobutane-2-sulfonate was prepared in 17.0 mL acetone. To this solution was added 0.2165 g HPMCAS-M polymer. The mixture was stirred overnight. This solution was spray dried using a small-scale spray-dryer, which consisted of an atomizer in the top cap of a vertically oriented 11-cm diameter stainless steel pipe. The atomizer was a two-fluid nozzle, where the atomizing gas was nitrogen delivered to the nozzle at 65° C. at a flow rate of 31 standard L/min (SLPM), and the solution to be spray dried was delivered to the nozzle at room temperature at a flow rate of 1.3 mL/min using a syringe pump. The outlet temperature of the drying gas and evaporated solvent was 30.5° C. Filter paper (11 micron Whatman® #1) with a supporting screen was clamped to the bottom end of the pipe to collect the solid spray-dried material and allow the nitrogen and evaporated solvent to escape.

Dispersion 2

A solution of 0.155 g erlotinib 1,4-bis(2-ethylhexoxy)-1,4-dioxobutane-2-sulfonate was prepared in 7.91 g methanol. To this solution was added 16.0 g methylene chloride followed by 0.2049 g HPMC E-3 polymer. The mixture was stirred overnight. The solution was then sprayed on a small-scale spray-dryer using the same conditions reported for Dispersion 1.

Control 1

Control 1 consisted of the crystalline form of erlotinib free base.

Dissolution of Dispersions 1 and 2, and Control 1

Dispersion 1 was evaluated in vitro using a microcentrifuge dissolution test using the following procedure. First, a sample of Dispersion 1 was placed in a microcentrifuge tube. A simulated gastric buffer (GB) solution consisting of 0.01 N HCl in water at 37° C. was added to each tube, so that the concentration if all of the active in the dispersion had dissolved would have been 2000 μg/mL. The tubes were vortexed for 1 minute. All work was performed in a temperature-controlled box at 37° C. After 9 minutes, the tubes were centrifuged at 13,000 rpm for 1 minute. A 50 μL centrifuged supernatant aliquot was removed from each tube and added to an HPLC vial containing 250 μL HPLC grade methanol. Following sample removal, the tubes were vortexed for 30 seconds. The tubes were allowed to sit undisturbed until the next sample, repeating the centrifuging/sampling/vortexing steps described above, to obtain a sample at 25 minutes following addition of the GB solution to the sample.

After 30 minutes in the GB solution, 0.8 mL of double strength (1 wt %) simulated intestinal fluid powder (SIF powder, available from Phares AG, Basel, Switzerland) in double strength phosphate buffer saline (0.166 M NaCl, 0.040 M $Na_2HPO_4$, and 0.093 M $KH_2PO_4$), adjusted to pH 6.5 was added to each tube. The tubes were vortexed for 1 minute. The testing solution composition was used to model fasted simulated intestinal fluid (FaSSIF). The FaSSIF powder contains bile salts (taurocholate) and phospholipids (lecithin) in a molar ratio of 4 to 1, along with buffers and osmotic adjusters. The concentration of active in each tube was 1000 μg/mL if all of the active had dissolved. After 3 minutes in the FaSSIF solution, the tubes were centrifuged at 13,000 rpm for 1 minute. A 50 μL centrifuged supernatant aliquot was removed, as previously described, and added to an HPLC vial containing 250 μL of methanol. The tube then was vortexed for 30 seconds, and left undisturbed until the next time point. The procedure was repeated to collect samples at 10, 20, 40, 90, and 180 minutes after addition of FaSSIF to the vials.

The dissolved concentrations of active were measured by HPLC. HPLC was performed using a Zorbax® SB-C18, 4.6×150 mm, 5 μm column at 30° C., and a mobile phase comprising 20 mM ammonium acetate/acetonitrile (43/57 vol/vol). The flow rate was 1.0 mL/min, 10 μL of each solution was injected, and the absorbance was measured at 332 nm.

Dispersion 2 was tested using the same procedures described above. The results are presented in Table 1. Control 1 was tested using the same procedures described above. The results are also presented in Table 1.

TABLE 1

| Time (minutes) | Dissolved Active Concentration (μg/mL) | | |
|---|---|---|---|
| | Dispersion 1 | Dispersion 2 | Control 1 |
| 0 | Start of GB Dissolution | | |
| 10 | 0.00 | 192.8 | 1,847.8 |
| 25 | 0.00 | 85.2 | 1,818.5 |
| 30 | Addition of FaSSIF Solution | | |
| 34 | 650.6 | 257.1 | 58.0 |
| 40 | 635.0 | 315.1 | 68.1 |
| 50 | 635.2 | 230.7 | 51.4 |
| 70 | 196.2 | 230.4 | 55.1 |
| 120 | 163.0 | 134.8 | 67.8 |
| 210 | 150.5 | 128.2 | 55.1 |

The results show that Dispersion 1 showed no dissolved active concentration during exposure to the GB solution, but showed a 2.4-fold dissolved active concentration after 120 minutes (90 minutes after addition of the FaSSIF solution) relative to Control 1. Dispersion 2 showed a 2-fold dissolved active concentration after 120 minutes relative to Control 1. These data demonstrate the utility of the compositions of the invention.

Embodiments of a composition include a solid dispersion comprising (a) a dispersion polymer, (b) a basic low-water solubility active having a pKa, wherein the active in the solid dispersion is substantially non-crystalline, and (c) an anionic counterion for the active, wherein the dispersion polymer, the active, and the anionic counterion collectively constitute at least 50 wt % of the solid dispersion, wherein the anionic counterion counterion has a molecular weight of at least 200 Daltons, a Log P value of at least 2, and a pKa that is at least 1.5 units less than the highest pKa of the active, and the composition comprises at least 80% of a stoichiometric amount of the anionic counterion to form a salt form with the active.

In any or all of the above embodiments, the active and the anionic counterion may form a salt form. In some embodiments, the salt form in pure form has a melt temperature that is 10° C. less than a melt temperature of an HCl salt form of the active and/or a melt temperature that is 10° C. less than a melt temperature of a free base of the active in pure form. In any or all of the foregoing embodiments, the salt form in pure form may be substantially non crystalline.

In any or all of the above embodiments, the anionic counterion may have a molecular weight of at least 400 Daltons. In any or all of the above embodiments, the anionic counterion may have a Log P value of at least 3. In any or all of the above embodiments, the anionic counterion has a pKa that is at least 2 units less than the highest pKa of the active. In any or all of the above embodiments, the salt form may have an aqueous solubility, when measured in an aqueous solution containing 0.01 M HCl at pH 2.0 at 37° C., that is lower than an aqueous solubility of a HCl salt of the active when measured in an aqueous solution containing 0.01 M HCl at pH 2.0 at 37° C.

In any or all of the above embodiments, the anionic counterion may comprise at least 8 carbon atoms, and at least one acidic group. In any or all of the above embodiments, the anionic counterion may comprise at least 18 carbon atoms, and at least one group selected from sulfate, phosphate, and carboxylate. In any or all of the above embodiments, the anionic counterion may be 1,4-bis(2-ethylhexoxy)-1,4-dioxobutane-2-sulfonate, cholesteryl sulfate, cholesteryl phosphate, tocopherol sulfate, tocopherol phosphate, 4,4'-methylenebis(3-hydroxy-2-naphthoic acid), 2,6-di-tert-butylnaphthalene-1-sulfonic acid, 2,6-di-tert-butylnaphthalene-1,5-disulfonic acid, 1,4-dicyclohexyloxy-1, 4-dioxobutane-2-sulfonic acid, 1,4-diisopentyloxy-1,4-dioxobutane-2-sulfonic acid, or any combination thereof.

In any or all of the above embodiments, the dispersion polymer may be hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose (HPMC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), dextran, dextran acetate, dextran propionate, dextran succinate, dextran acetate propionate, dextran acetate succinate, dextran propionate succinate, dextran acetate propionate succinate, polyvinylpyrrolidone (PVP), polyvinylpyrrolidone polyvinyl acetate copolymer (PVP-VA), poly(methacrylic acid-co-methyl methacrylate) 1:1, poly(methacrylic acid-co-methyl methacrylate) 1:2, poly(methacrylic acid-co-ethyl acrylate) 1:1, or any combination thereof.

In any or all of the above embodiments, the composition may comprise at least a stoichiometric amount of the anionic counterion to form the salt form with the active. In any or all of the above embodiments, the composition may comprise a stoichiometric excess of the amount of the anionic counterion to form the salt form with the active.

Embodiments of a process for making the disclosed compositions include forming a spray solution comprising a basic low-water solubility active, an anionic counterion, a dispersion polymer, and a solvent, and spray drying the spray solution to form a dry powder. Embodiments of the process may be used to make a product. In some embodiments, the product comprises a composition made by the process and an excipient.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A composition comprising a solid dispersion, said solid dispersion comprising:
   (a) a basic low-water solubility active having a pKa and an anionic counterion of said active; and
   (b) a polymer in which the basic low-water solubility active and the anionic counterion are dispersed, wherein the polymer is hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose (HPMC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), dextran, dextran acetate, dextran propionate, dextran succinate, dextran acetate propionate, dextran acetate succinate, dextran propionate succinate, dextran acetate propionate succinate, polyvinylpyrrolidone (PVP), polyvinylpyrrolidone polyvinyl acetate copolymer (PVP-VA), poly(methacrylic acid-co-methyl methacrylate) 1:1, poly(methacrylic acid-co-methyl methacrylate) 1:2, poly(methacrylic acid-co-ethyl acrylate) 1:1, or any combination thereof;
   wherein said active in said solid dispersion is about 90 wt % or greater non-crystalline,
   wherein said polymer, said active, and said anionic counterion collectively constitute about 50 wt % or greater of said solid dispersion,
   wherein said anionic counterion has a molecular weight of at least 200 Daltons, a Log P value of at least 2, and a pKa that is at least 1.5 units less than the highest pKa of said active, and
   wherein the composition comprises about 80% or greater of a stoichiometric amount of said anionic counterion to form a salt form with said active.

2. The composition of claim 1, wherein said anionic counterion has a molecular weight of at least 400 Daltons.

3. The composition of claim 1, wherein said anionic counterion has a Log P value of at least 3.

4. The composition of claim 1, wherein said anionic counterion has a pKa that is at least 2 units less than the highest pKa of said active.

5. The composition of claim 1, wherein said salt form has an aqueous solubility, when measured in an aqueous solution containing 0.01 M HCl at pH 2.0 at 37° C., that is lower than an aqueous solubility of a free base of said active when measured in an aqueous solution containing 0.01 M HCl at pH 2.0 at 37° C.

6. The composition of claim 1, wherein said anionic counterion comprises at least 8 carbon atoms, and at least one acidic group.

7. The composition of claim 1, wherein said anionic counterion comprises at least 18 carbon atoms, and at least one group selected from sulfate, phosphate, and carboxylate.

8. The composition of claim 1, wherein said anionic counterion is 1,4-bis(2-ethylhexoxy)-1,4-dioxobutane-2-sulfonate, cholesteryl sulfate, cholesteryl phosphate, tocopherol sulfate, tocopherol phosphate, 4,4'-methylenebis(3-hydroxy-2-naphthoic acid), 2,6-di-tert-butylnaphthalene-1-sulfonic acid, 2,6-di-tert-butylnaphthalene-1,5-disulfonic acid, 1,4-dicyclohexyloxy-1,4-dioxobutane-2-sulfonic acid, 1,4-diisopentyloxy-1,4-dioxobutane-2-sulfonic acid, or any combination thereof.

9. The composition of claim 1, wherein said salt form in pure form has a melt temperature that is 10° C. less than a melt temperature of an HCl salt form of said active.

10. The composition of claim 1, wherein said salt form in pure form has a melt temperature that is 10° C. less than a melt temperature of a free base of said active in pure form.

11. The composition of claim 1, wherein said salt form in pure form is about 90 wt % or greater non crystalline.

12. The composition of claim 1, comprising at least a stoichiometric amount of the anionic counterion to form the salt form with said active.

13. The composition of claim 1, comprising a stoichiometric excess of the amount of the anionic counterion to form the salt form with said active.

14. A process of making the composition of claim 1, comprising:
   (a) forming a spray solution comprising (i) a salt form of the basic low-water solubility active and the anionic counterion, (ii) the polymer, and (iii) a solvent; and
   (b) spray drying said spray solution to form a dry powder.

15. A product made by the process of claim 14.

16. A product, comprising:
   a composition made by the process of claim 14; and
   an excipient.

17. A composition comprising a solid dispersion, the solid dispersion comprising:
   (a) a basic low-water solubility active having a pKa and an anionic counterion of the active; and
   (b) a polymer in which the basic low-water solubility active and the anionic counterion are dispersed, wherein the polymer is polyvinyl pyrrolidone (PVP), polyethyleneoxide (PEO), polyethylene glycol (PEG), poly(vinyl pyrrolidone-co-vinyl acetate) (PVP-VA), a polyoxyethylene-polyoxypropylene block copolymer, a graft copolymers comprised of polyethylene glycol, polyvinyl caprolactam and polyvinyl acetate, a polymethacrylate, a polyoxyethylene alkyl ether, a polyoxyethylene castor oil, polycaprolactam, polylactic acid, polyglycolic acid, poly(lactic-glycolic)acid, a lipid, cellulose, pullulan, dextran, maltodextrin, hyaluronic acid, polysialic acid, chondroitin sulfate, heparin, fucoidan, pentosan polysulfate, spirulan, hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose (HPMC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), dextran, dextran acetate, dextran propionate, dextran succinate, dextran acetate propionate, dextran acetate succinate, dextran propionate succinate, dextran acetate propionate succinate, poly(methacrylic acid-co-methyl methacrylate) 1:1, poly(methacrylic acid-co-methyl methacrylate) 1:2, poly(methacrylic acid-co-ethyl acrylate) 1:1, or any combination thereof;

wherein the active in the solid dispersion is about 90 wt % or greater non-crystalline, wherein the anionic counterion, when associated with the active, is about 90 wt % or greater non-crystalline, wherein the polymer, the active, and the anionic counterion collectively constitute about 50 wt % or greater of the solid dispersion, wherein the anionic counterion has a molecular weight of at least 200 Daltons, a Log P value of at least 2, and a pKa that is at least 1.5 units less than the highest pKa of the active, and wherein the composition comprises about 80% or greater of a stoichiometric amount of the anionic counterion to form a salt form with the active.

18. The composition of claim 17 wherein the polymer is HPMCAS, HPMCP, CAP, CAT, methyl cellulose acetate phthalate, hydroxypropyl cellulose acetate phthalate, cellulose acetate terephthalate, cellulose acetate isophthalate, CMEC, HPMC, HPMCAP, hydroxypropyl methylcellulose propionate phthalate, HPMCAT, hydroxypropyl methylcellulose propionate trimellitate, CAS, MCAS, dextran, dextran acetate, dextran propionate, dextran succinate, dextran acetate propionate, dextran acetate succinate, dextran propionate succinate, dextran acetate propionate succinate, PVP, PVP-VA, poly(methacrylic acid-co-methyl methacrylate) 1:1, poly(methacrylic acid-co-methyl methacrylate) 1:2, poly(methacrylic acid-co-ethyl acrylate) 1:1, or any combination thereof.

19. The composition of claim 17, wherein the salt form of the active and the anionic counterion in pure form has an aqueous solubility, when measured in an aqueous solution containing 0.01 M HCl at pH 2.0 at 37° C., that is (i) less than about 0.9-fold an aqueous solubility of a free base of the active when measured in an aqueous solution containing 0.01 M HCl at pH 2.0 at 37° C., (ii) less than about 0.9-fold an aqueous solubility of a HCl salt form of the active when measured in an aqueous solution containing 0.01 M HCl at pH 2.0 at 37° C., or both (i) and (ii).

\* \* \* \* \*